US010781195B2

(12) United States Patent
Dumesic et al.

(10) Patent No.: US 10,781,195 B2
(45) Date of Patent: Sep. 22, 2020

(54) PROCESS TO PRODUCE 5-HYDROXYMETHYLFURFURAL (HMF) FROM CARBOHYDRATES USING A SOLVENT SYSTEM CONTAINING WATER AND A POLAR APROTIC SOLVENT

(71) Applicant: Wisconsin Alumni Research Foundation, Madison, WI (US)

(72) Inventors: James A. Dumesic, Verona, WI (US); Ali Hussain Motagamwala, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/050,522

(22) Filed: Jul. 31, 2018

(65) Prior Publication Data

US 2020/0039947 A1 Feb. 6, 2020

(51) Int. Cl.
*C07D 307/50* (2006.01)
(52) U.S. Cl.
CPC .................. *C07D 307/50* (2013.01)
(58) Field of Classification Search
CPC .................................................. C07D 307/50
See application file for complete search history.

(56) References Cited

FOREIGN PATENT DOCUMENTS

EP 2985280 A1 * 2/2016 ........... C07D 307/50

OTHER PUBLICATIONS

Wade, L. G. "Organic Chemistry 2013" Pearson, Chapter 1; p. 23.*
Cinlar, B., "Kinetics of monosaccharide conversion in the presence of homogeneous Bronsted acids." Applied Catalysis A: General 450 (2013): 237-242.*
Qi, X., "Catalytic dehydration of fructose into 5-hydroxymethylfurfural by ion-exchange resin in mixed-aqueous system by microwave heating." Green Chemistry 10.7 (2008): 799-805.*
Corma, A. , "Chemical routes for the transformation of biomass into chemicals." Chemical reviews 107.6 (2007): 2411-2502.*
Karinen, R., "Biorefining: heterogeneously catalyzed reactions of carbohydrates for the production of furfural and hydroxymethylfurfural." ChemSusChem 4.8 (2011): 1002-1016.*
Kulkarni, P., "Methane Sulphonic Acid is Green Catalyst in Organic Synthesis." Oriental Journal of Chemistry 31.1 (2015): 447-451.*
Jeong, J., "Commercially attractive process for production of 5-hydroxymethyl-2-furfural from high fructose corn syrup." Journal of Industrial and Engineering Chemistry 19.4 (2013): 1106-1111.*
White, J.S.,"Straight talk about high-fructose corn syrup: what it is and what it ain't." The American journal of clinical nutrition 88.6 (2008): 1716S-1721S.*
Román-Leshkov, Y.,"Solvent effects on fructose dehydration to 5-hydroxymethylfurfural in biphasic systems saturated with inorganic salts." Topics in Catalysis 52.3 (2009): 297-303.*

Alamillo et al., The Selective hydrogenation of biomass-derived 5-hdroxymethylfurfual using heterogeneous catalysts, *Green Chem.* 2012, 14, 1413-1419.
Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical. Chemistry B*, 102:10817-10825.
Binder et al., Simple Chemical Transformation of Lignocellulosic Biomass into Furans for Fuels and Chemicals, *J. Am. Chem. Soc.* 2009, 131, 1979-1985.
Dutta et al., A Brief Summary of the Synthesis of Polyester Building-Block Chemicals and Biofuels from 5-Hydroxymethylfurfural, *ChemPlusChem* 2012, 77, 259-272.
Li et al., Production of 5-hydroxymethylfurfural in ionic liquids under high fructose concentration conditions, *Carbohydr. Res.* 2010, 345, 1846-1850.
Rinaldi et al., Depolymerization of Cellulose Using solid Catalysts in Ionic Liquids, *Angewandte Chemie-International Edition* 2008, 47, 8047-8050.
Rinaldi et al., Acid Hydrolysis of Cellulose as the Entry Point into Biorefinery Schemes, *ChemSusChem* 2009, 2, 1096-1107.
Roman-Leshkov et al., Phase Modifiers Promote Efficient Production of Hydroxymethylfurfural from Fructose, *Science* 2006, 312, 1933-1937.
Roman-Leshkov et al., Production of dimethylfuran for liquid fuels from biomass-derived carbohydrates, *Nature* 2007, 447, 982-985.
Roman-Leshkov et al., Solvent Effects on Fructose Dehydration to 5-Hydroxymethylfurfual in Biphasic systems Saturated with Inorganic Salts, *Topics in Catalysis* 2009, 52, 297-303.
Sen et al., Conversion of biomass to sugars via ionic liquid hydrolysis: process synthesis and economic evaluation, *Biofuels, Bioproducts and Biorefining* 2012, 6, 444-452.
Shen et al., Hydrochloric Acid-Catalyzed Levulinic Acid Formation from Cellulose: Data and Kinetic Model to Maximize Yields, *AIChE J.* 2012, 58, 236-246.
Wang et al., Selective Production of Aromatics from Alkylfurans over Solid Acid Catalysts, *Chemcatchem* 2013, 5, 2044-2050.
Van De Vyver et al., Catalytic production of levulinic acid from cellulose and other biomass-derived carbohydrates with sulfonated hyperbranched poly(arlene oxindole)s, *Energy Environ. Sci.* 2011, 4, 3601-3610.
Van Putten et al., Hydroxymethylfurfural, A Versatile Platform Chemical Made from Renewable Resources, *Chem. Rev.* 2013, 113, 1499-1597.
Vigier et al., Conversion of fructose and insulin to 5-hydroxymethylfurfural in sustainable betaine hydrochloride-based media, *Green Chem.* 2012, 14, 285-289.

(Continued)

*Primary Examiner* — John M Mauro
(74) *Attorney, Agent, or Firm* — Joseph T. Leone, Esq.; Dewitt LLP

(57) ABSTRACT

A method to produce 5-hydroxymethylfurfural (HMF) from C6 carbohydrates. The method includes the steps of reacting a reactant comprising at least one C6 carbohydrate, in a reaction mixture comprising at least about 5% (v/v) water, a polar, aprotic solvent, and an acid, for a time, at a temperature, and at a hydrogen ion concentration wherein at least a portion of the C6 carbohydrate present in the reactant is converted to 5-hydroxymethyl furfural ("HMF").

18 Claims, 16 Drawing Sheets

(56) References Cited

OTHER PUBLICATIONS

Yin et al., Hydrothermal Conversion of Cellulose to 5-Hydroxymethyl Furfural, *Int. J. Green Energy* 2011, 8, 234-247.
Zakrzewska et al., Ionic Liquid-Mediated Formation of 5-Hydroxymethylfurfual—A Promising Biomass-Derived Building Block, *Chem. Rev.* 2011, 111, 397-417.
Zhang et al., An Unexpected Reaction between 5-Hydroxymethylfurfural and Imidazolium-Based Ionic Liquids at High Temperatures, *Molecules* 2011, 16, 8463-8474.
Zhao et al., Metal Chlorides in Ionic Liquid Solvents Convert sugars to 5-Hydroxymethylfurfural, *Science* 2007, 316, 1597-1600.

\* cited by examiner

PROCESS TO PRODUCE 5-HYDROXYMETHYLFURFURAL (HMF) FROM CARBOHYDRATES USING A SOLVENT SYSTEM CONTAINING WATER AND A POLAR APROTIC SOLVENT

FEDERAL FUNDING STATEMENT

This invention was made with government support under DE-FC02-07ER64494 awarded by the US Department of Energy. The government has certain rights in the invention.

BACKGROUND

5-Hydroxymethyl furfural (HMF) is an alternative, non-petroleum precursor which can be used as a building block chemical for producing various high-volume and value-added organic chemicals. These chemicals include 2,5-furandicarboxylic acid (FDCA) which can serve as a precursor in the polymer industry, and 2,5-dimethylfuran (DMF) which can be used as a liquid transportation fuel. See S. Dutta, S. De, B. Saha, *ChemPlusChem* 2012, 77, 259-272 and Y. Roman-Leshkov, C. J. Barrett, Z. Y. Liu, J. A. Dumesic, *Nature* 2007, 447, 982-985. DMF can also be used to produce p-xylene via cycloaddition with ethylene combined with dehydration over acidic zeolites and acidic oxides. (D. Wang, C. M. Osmundsen, E. Taarning, J. A. Dumesic, *Chemcatchem* 2013, 5, 2044-2050.) Alamillo et al. have shown quantitative yields of 2,5-di-hydroxy-methyl-tetrahydrofuran from HMF with ruthenium-supported oxide catalysts. R. Alamillo, M. Tucker, M. Chia, Y. Pagan-Torres, J. Dumesic, *Green Chem.* 2012, 14, 1413-1419.

HMF is produced conventionally from glucose (in low yields) or fructose (in high yields) by a triple dehydration step with mineral acids in water. J. C. Shen, C. E. Wyman, *Aiche J.* 2012, 58, 236-246. It would be highly desirable to be able to produce HMF from cellulose, which is a more abundant and lower value feedstock than fructose. However, in aqueous systems, HMF is only produced in low yields (between 8 to 21%) from cellulose because of miscibility limitations and undesired formation of humins. S. D. Yin, Y. L. Pan, Z. C. Tan, *Int. J. Green Energy* 2011, 8, 234-247. HMF production is maximized at relatively high temperatures (200-300° C.) and short reaction times (on the order of seconds or minutes). In aqueous systems, HMF is readily converted to formic acid and levulinic acid. The latter compound is also a versatile, bio-based platform chemical. S. Van de Vyver, J. Thomas, J. Geboers, S. Keyzer, M. Smet, W. Dehaen, P. A. Jacobs, B. F. Sels, *Energy Environ. Sci.* 2011, 4, 3601-3610.

The use of ionic liquids (ILs) as solvents for HMF production has been proposed due to the solvation capabilities of the ILs. A HMF yield of 51% from fructose was obtained by Li et al. when a high concentration of feed (67 wt %) was used in 1-butyl-3-methylimidazolium chloride. C. Li, Z. K. Zhao, A. Wang, M. Zheng, T. Zhang, *Carbohydr. Res.* 2010, 345, 1846-1850. Binder and Raines developed a process to convert lignocellulosic biomass to HMF using N,N-dimethylacetamide (DMA) containing lithium chloride as a solvent. J. B. Binder, R. T. Raines, *J. Am. Chem. Soc.* 2009, 131, 1979-1985. HMF yields of up to 54% were obtained with 1-ethyl-3-methylimidazolium chloride as an additive and a mixture of $CrCl_2/HCl$ as the catalyst. Rinaldi et al. showed that solid acid catalysts can be used in 1-butyl-3-methylimidazolium chloride to selectively depolymerize cellulose to produce glucose and HMF. R. Rinaldi, R. Palkovits, F. Schuth, *Angewandte Chemie-International Edition* 2008, 47, 8047-8050. Zhang and co-workers have reported HMF yields of 55% from cellulose with a mixture of $CuCl_2$ and $CrCl_2$ dissolved in 1-ethyl-3-methylimidazolium chlorid at relatively low temperatures. H. Zhao, J. E. Holladay, H. Brown, Z. C. Zhang, *Science* 2007, 316, 1597-1600. A comprehensive review covering the process chemistry of HMF production from various feedstocks is given by van Putten et al. R. J. van Putten, J. C. van der Waal, E. de Jong, C. B. Rasrendra, H. J. Heeres, J. G. de Vries, *Chem. Rev.* 2013, 113, 1499-1597.

Significant challenges hinder the industrial use of ILs for production of HMF. Due to their high costs, quantitative recovery and recycling of ILs (at least 98%) is necessary to make the process economically attractive. S. M. Sen, J. B. Binder, R. T. Raines, C. T. Maravelias, *Biofuels, Bioproducts and Biorefining* 2012, 6, 444-452. Relative low cellulose solubility (10-15 wt %) in ILs, high viscosity, and high toxicity of ILs are also impeding factors. R. Rinaldi, F. Schuth, *ChemSusChem* 2009, 2, 1096-1107 and M. E. Zakrzewska, E. Bogel-Łukasik, R. Bogel-Łukasik, *Chem. Rev.* 2011, 111, 397-417. Thermal and chemical stabilities of ILs are also in question, as new compounds have been detected derived from side reactions between HMF and imidazolium-based ILs. Z. Zhang, W. Liu, H. Xie, Z. K. Zhao, *Molecules* 2011, 16, 8463-8474. Extensive work has been reported by Jerome and co-workers to produce HMF from biomass derived feedstock in alternative solvent systems that are comparable with imidazolium-based ILs. K. D. Vigier, A. Benguerba, J. Barrault, F. Jerome, *Green Chem.* 2012, 14, 285-289. Alternative approaches have also been investigated using biphasic reaction systems with organic solvents that can extract the HMF from the aqueous phase before it undergoes further degradation reactions. Y. Roman-Leshkov, J. N. Chheda, J. A. Dumesic, *Science* 2006, 312, 1933-1937. Phase modifiers (e.g., NaCl) can be added to the aqueous phase to help enhance HMF partitioning into the immiscible organic phase and consequently impede further HMF degradation. Y. Roman-Leshkov, J. A. Dumesic, *Topics in Catalysis* 2009, 52, 297-303.

There thus remains a long-felt and unmet need for an easy, fast, and economical method to produce HMF from carbohydrates.

SUMMARY OF THE INVENTION

Disclosed herein is a method to produce 5-hydroxymethylfurfural (HMF). The method comprise reacting a reactant comprising at least one C6 carbohydrate, in a reaction mixture comprising at least about 5% (v/v) water, a polar aprotic solvent, and an acid. The reaction is carried out for a time, at a temperature, and at a hydrogen ion concentration wherein at least a portion of the C6 carbohydrate present in the reactant is converted to 5-hydroxymethyl furfural ("HMF").

The acid may be present in an amount to yield a hydrogen ion concentration in the reaction mixture of from about 5 mM to about 500 mM, or from about 5 mM to about 100 mM, or from about 5 mM to about 50 mM. The acid may be a Brønsted-Lowry acid, or a mineral acid, a solid acid, an organic acid, or any combination thereof.

In all versions of the method, it is preferred, but not required, that the reaction be carried out at a temperature of from about 80° C. to about 300° C., or from about 80° C. to about 250° C., or from about 80° C. to about 220° C., or from about 100° C. to about 200° C. Reaction temperatures above and below these ranges are within the scope of the disclosure.

The polar, aprotic solvent is preferably selected from the group consisting of symmetrical or unsymmetrical di-$C_1$-$C_6$-alkyl ketones, such as acetone, diethyl ketone, methylethyl ketone, and the like. The preferred aprotic solvent is acetone.

It is generally preferred that the polar, aprotic solvent is present in a concentration of from about 75% (v/v) to about 95% (v/v) in water, and most preferred that the polar, aprotic solvent is present in a concentration of about 80% (v/v) in water.

The at least one C6 carbohydrate used as the reactant preferably comprises fructose. The reactant may also comprise a mixture of two or more of fructose, glucose, and mannose.

Another version of the method comprises reacting a reactant comprising glucose and fructose, in a reaction mixture comprising from about 5% to about 30% (v/v) water, from about 95% to about 70% (v/v) polar, aprotic solvent, and an acid, for a time, at a temperature, and at a hydrogen ion concentration wherein at least a portion of the fructose present in the reactant is converted to 5-hydroxymethyl furfural ("HMF"). The ranges noted above with respect to hydrogen ion concentration, solvent concentrations, etc., apply to this version of the method as well.

DETAILED DESCRIPTION

Abbreviations and Definitions

Figure 1A:
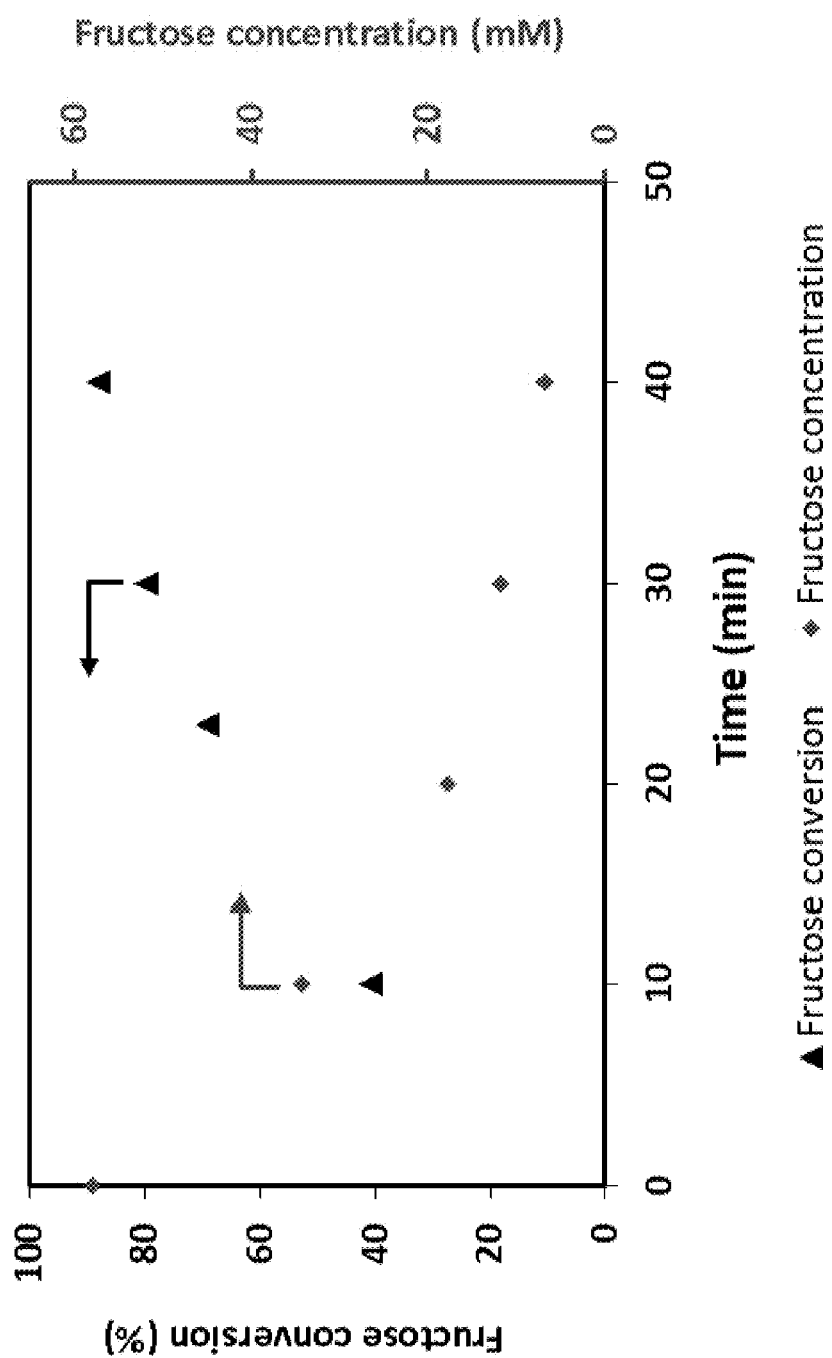
FIG. 1A is a graph showing fructose conversion and fructose concentration over time using the dehydration method disclosed herein with a feedstock comprising 5 wt % fructose. Reaction conditions: 125° C.; reactant was 5 wt % fructose in water and the solvent system was 80%/20% acetone in water (v/v) (thus, the overall concentration of fructose was 1% after adding 20% acetone); 15 mM HCl; mixed at 500 rpm. Key: ▲=fructose conversion; ♦=fructose concentration.

HMF=5-hydroxymethyl furfural.

"Brønsted-Lowry Acid/Base"=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"C6 carbohydrate" refers to any carbohydrate, without limitation, that has six (6) carbon atoms. The definition includes hexose sugars of any description and stereoisomerism (e.g., D/L aldohexoses and D/L ketohexoses). C6 carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5$)$_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Glucose-containing oligomers, glucose-containing polymers, Glucose-containing reactants, C6-containing reactant" refers to any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Polar, aprotic solvent" refers to any solvent having a net positive dipole moment, a relatively high dielectric constant, and which lacks a labile (acidic) hydrogen atom. Examples of polar, aprotic solvents include, but are not limited to, dichloromethane, hydrofurans (e.g. tetrahydrofuran), hydropyrans, ethylacetate, di-alkyl ketones such as acetone, methyl ethyl ketone, n-butanol etc., dimethylformamide, acetonitrile, dimethylsulfoxide, propylene carbonate, N-methyl-2-pyrrolidone, hexamethylphosphoramide, and the like.

"Ketone" as used herein refers to an organic compound with the structure RC(=O)R', where R and R' can be a variety of carbon-containing substituents. Ketone may be symmetrical or asymmetrical. Thus, as used herein, the term "ketone" explicitly includes (without limitation) diketone, saturated ketone, unsaturated ketone and cyclic ketone. Some ketones are miscible in water, such as acetone; other ketones have more limited solubility in water, such as cyclopentanone. Those ketones that can dissolve at least about 1 wt % water, and more preferably at least about 5 wt % (or more) of water (up to miscible) are suitable for use in the process described herein. Acetone is the most preferred ketone.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (⁻3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Lewis Acid/Base"=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula MX4; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzylzirconium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_n R'_m X_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MRnX3-n$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_n R'_m X_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_n R'_m X_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

"Mineral acid" refers to an acid derived from one or more inorganic compounds. Examples include, but are not limited to hydrochloric acid (HCl), nitric acid ($HNO_3$), phosphoric acid ($H_3PO_4$), sulfuric acid ($H_2SO_4$) boric acid ($H_3BO_3$), hydrofluoric acid (HF), hydrobromic acid (HBr), perchloric acid ($HClO_4$), and the like.

"Organic acid"=any organic acid, without limitation, such as toluenesulfonic acid, formic acid, acetic acid, trifluoroacetic acid, oxalic acid, furandicarboxylic acid and the like.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, silica-alumina, acid clays, sulfated zirconia, and phosphates such as zirconium phosphate, molecular sieve materials, zeolites, and acidic material on a thermally stable support. Where an acidic material is provided on a thermally stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

HMF Yield:

$$HMF\ Yield\ (\%) = \frac{moles\ of\ HMF\ produced}{initial\ moles\ of\ fructose\ in\ feed} \times 100$$

Selectivity:

$$HMF\ selectivity\ (\%) = \frac{moles\ of\ HMF\ produced}{moles\ of\ fructose\ reacted} \times 100$$

Reaction Rate:

$$Reaction\ rate\ (M/s) = \frac{d(total\ moles\ of\ carbohydrate\ reacted)}{dt}$$

The Method:

Disclosed herein is a method to produce HMF from C6 carbohydrates. As noted above, this includes the steps of reacting a reactant comprising at least one C6 carbohydrate, in a reaction mixture comprising at least about 5% (v/v) water, a polar, aprotic solvent, and an acid, for a time, at a temperature, and at a hydrogen ion concentration wherein at least a portion of the C6 carbohydrate present in the reactant is converted to 5-hydroxymethyl furfural ("HMF").

The C6 carbohydrate used in the method can be derived from any source, including from biomass (processed or unprocessed), cellulose, lignin and lignocellulosic sources, etc. The nature of the C6 carbohydrate is not critical to the method, although fructose is preferred, as a mixtures of at least two of fructose, glucose, and/or mannose. The method address key limitations of producing HMF using other solvent systems, such as gamma-valerolactone (GVL). HMF can be produced in GVL-containing solvent systems. However, it is very difficult to purify the HMF product from the GVL solvent. Notably, HMF has a boiling point of 114° C. and is thermally unstable. That render it impossible to separate HMF from GVL via distillation because GVL has a boiling point of 207° C. Liquid-liquid extraction of HMF from GVL is hampered by the fact that GVL and HMF have very similar solvation properties.

Figure 1B:
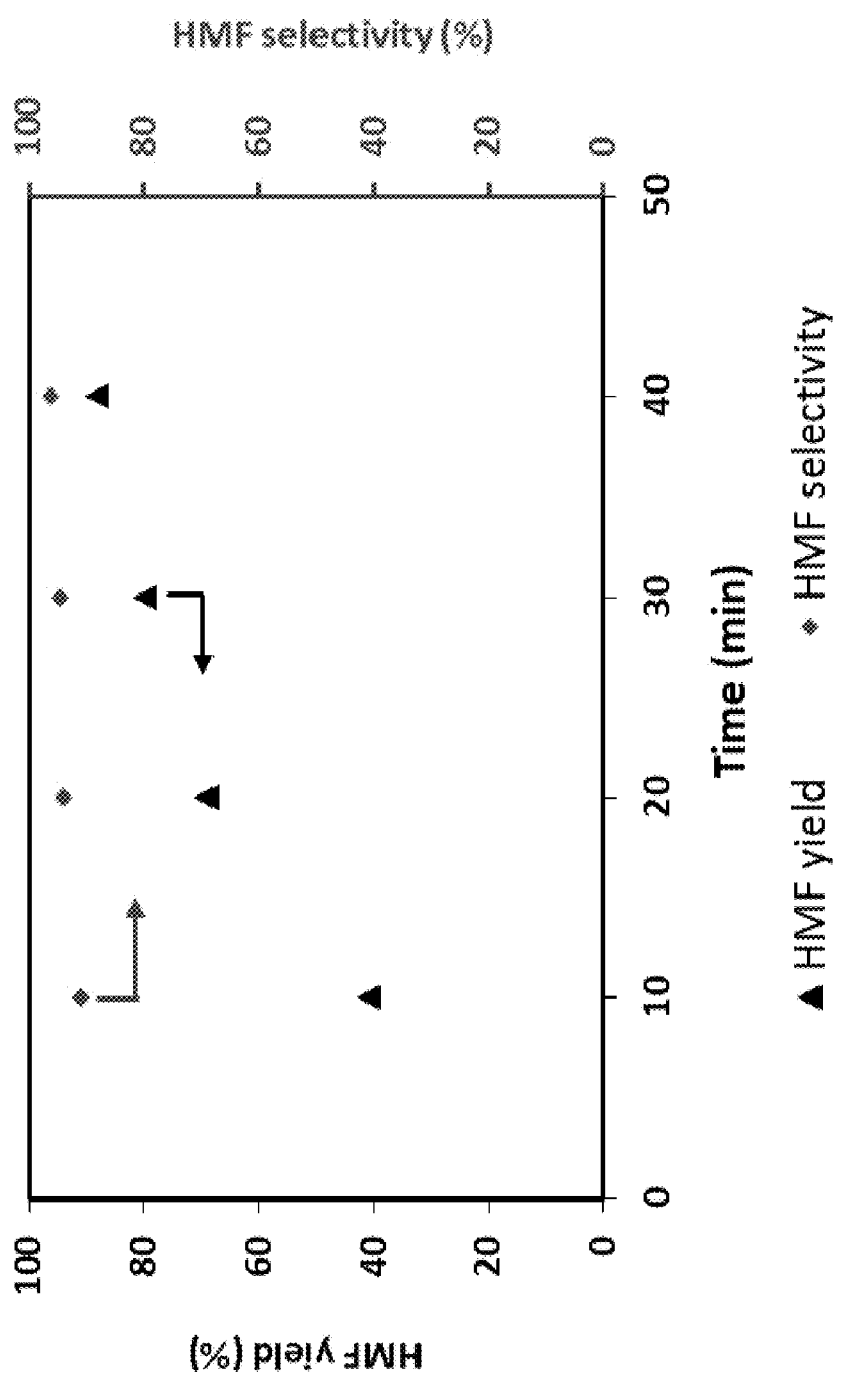
FIG. 1B is a graph showing HMF yield (%) and HMF selectivity (%) over time for the reaction described in FIG. 1A. Key: ▲=HMF yield; ♦=HMF selectivity.

It has been unexpectedly found that solvent systems comprising water and a polar, aprotic solvent, are ideally suited for converting C6 carbohydrates into HMF and reasonably low temperatures, low acid concentration and at very high yields and efficiencies. This is exemplified in the reaction whose results are depicted in FIGS. 1A and 1B. Here, fructose, at a relatively low concentration of 5 wt % (based on weight of water) was reacted at 125° C., with vigorous stirring, for 50 minutes in a solvent system comprising 80% acetone and 20% water (v/v). The reaction mix was acidified to 15 mM HCl and mechanically mixed at 500 rpm. The results were unexpectedly good. As shown in FIG. 1A, over the course of the 50 minute reaction, the fructose conversion was 88%, Fructose concentration dropped correspondingly. As shown in FIG. 1B, the yield of HMF was 85%. Selectivity to HMF was a very impressive 96%. In short, the reaction conditions disclosed herein generate very high HMF yield with even higher selectivity.

Figure 2:
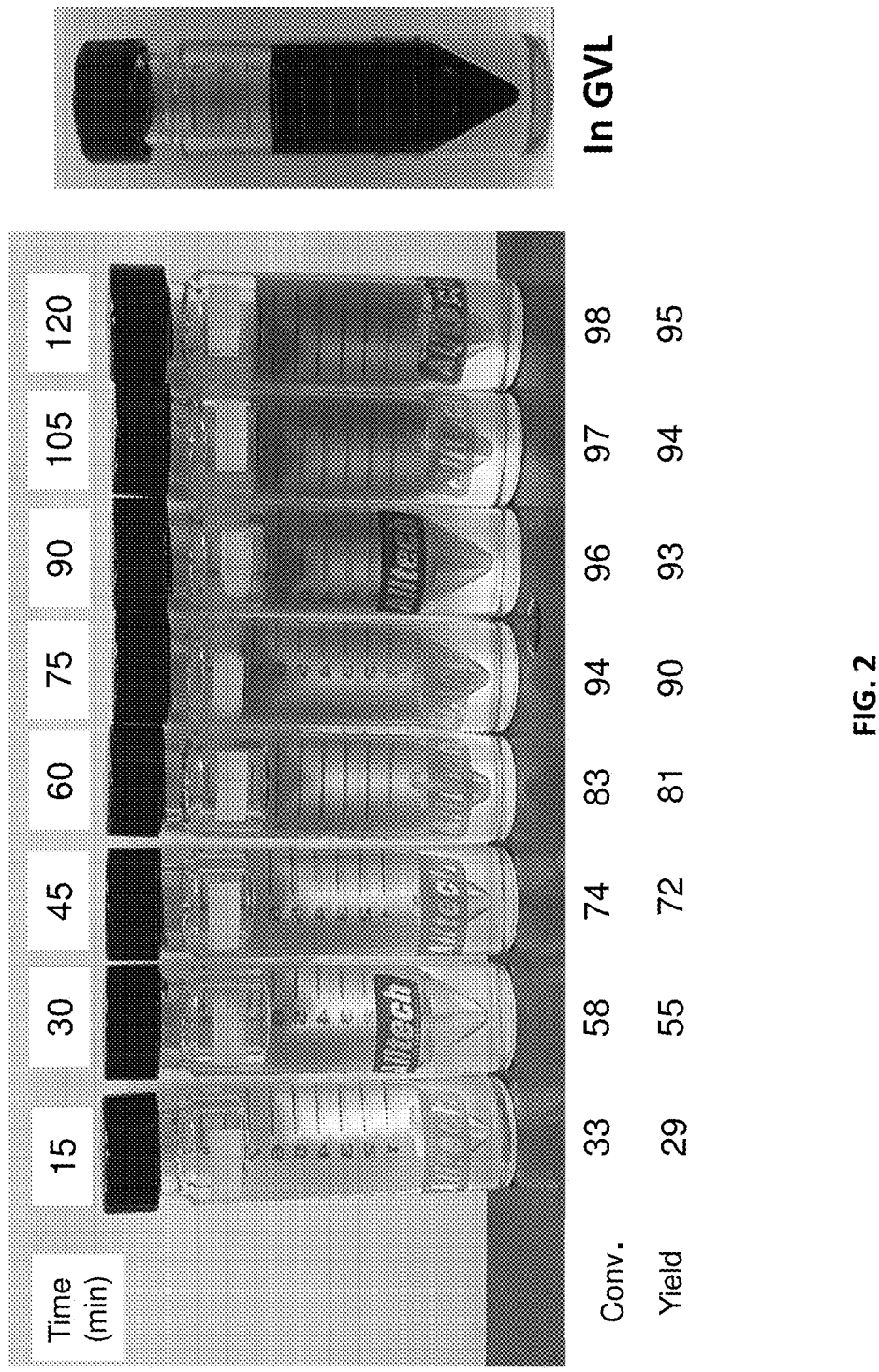
FIG. 2 is a series of photographs of the reaction solution over time for dehydration method disclosed herein using a feedstock comprising 5 wt % fructose. Reaction conditions: 125° C.; reactant was 5 wt % fructose; solvent system was 80%/20% acetone in water (v/v); 5 mM HCl; mixed at 500 rpm. Time points are given across the top of the figure; corresponding conversion and yield to HMF figures are given across the bottom of the figure. The far right shows the results of an analogous reaction using gamma-valerolactone (GVL) as the solvent.

This selectivity is best illustrated in FIG. 2, which is a series of time-lapse photographs of the reaction solution. The reaction that yielded the photographs in FIG. 2 used 5 wt % fructose, reacted at 125° C., in a solvent system of 80% acetone and 20% water (v/v), and 5 mM HCl, with vigorous mixing. Time points are given across the top of the figure; corresponding conversion and yield to HMF figures are given across the bottom of the figure. The far right shows the results of an analogous reaction using gamma-valerolactone (GVL) as the solvent. As can be seen in FIG. 2, the reaction solutions using the present method remain clear, without any tarry humins. The reaction solution at time point 120 minutes had a fructose conversion of 98% with a 95% yield to HMF. In contrast, when the same reaction is conducted using GVL as the solvent, the product is almost exclusively humins. See the far-right panel in FIG. 2.

The reaction is indifferent to the type of acid catalyst used. Reactions mirroring the conditions described above for FIGS. 1A and 1B were run with HCl, $H_2SO_4$, and methanesulfonic acid as acid catalyst. In each instance, fructose conversion, HMF yield and HMF selectivity were all above 90%. See Table 1.

TABLE 1

Fructose Dehydration - Effect of Acid Type

| Catalyst type | pKa | Fructose Conversion (%) | HMF Yield (%) | HMF Selectivity |
|---|---|---|---|---|
| HCl | −7 | 94.6 | 93.7 | 99.0 |
| $H_2SO_4$ | −3 | 95.7 | 93.1 | 97.3 |
| Methanesulfonic acid | −2.6 | 98.3 | 94.7 | 96.3 |

This is notable because methanesulfonic acid is significantly less corrosive than HCl and $H_2SO_4$, but is just as effective in the reaction as are the mineral acids. This in turn has a significant impact on reactor design and process economics because the reaction can be run under milder conditions.

Figure 3:
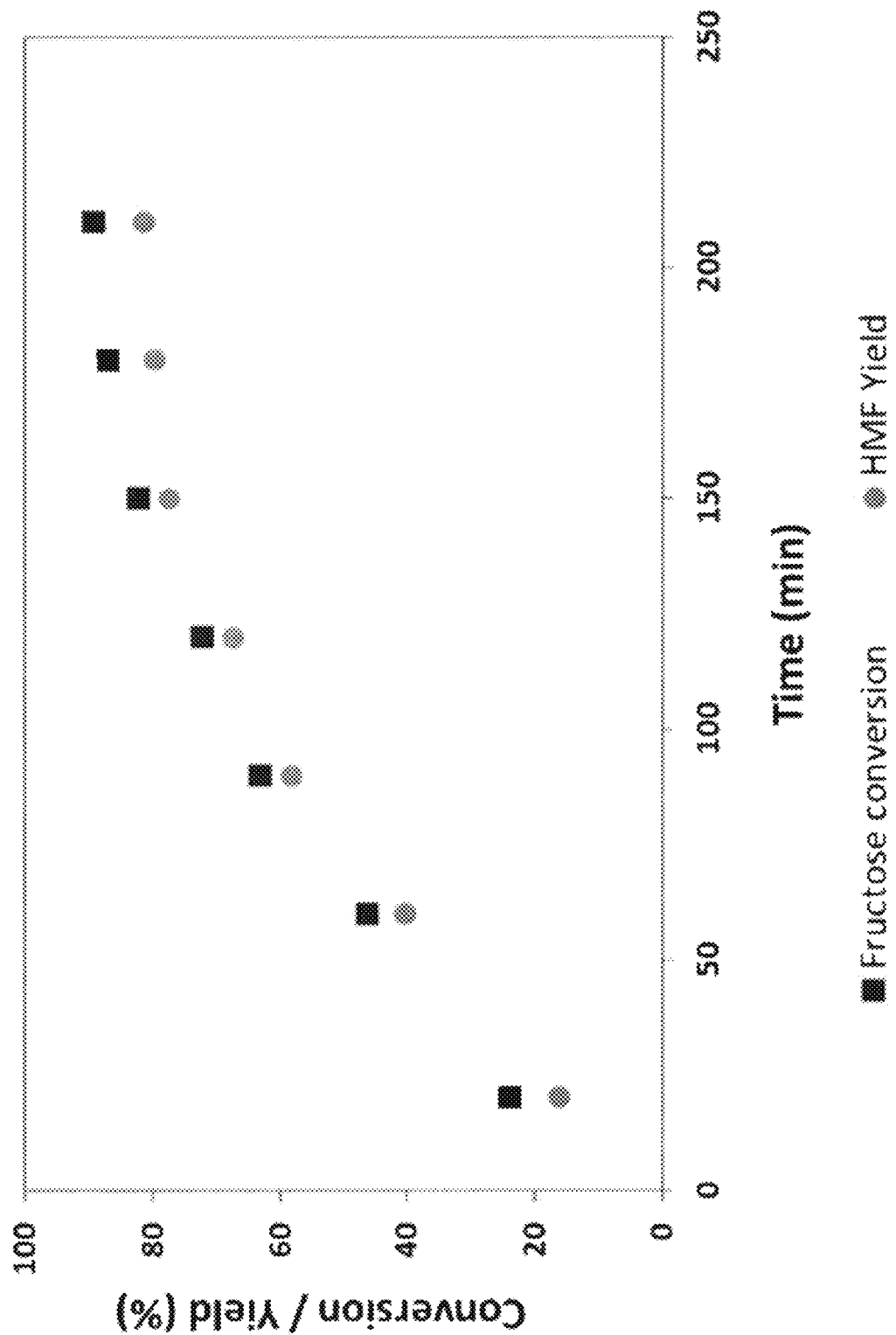
FIG. 3 is a graph showing fructose conversion and HMF yield over time using the dehydration method disclosed herein with a feedstock comprising 5 wt % fructose and a solid acid catalyst (Amberlyst®-brand sulfonic acid-type resin). Reaction conditions: 125° C.; reactant was 5 wt % fructose; solvent system was 80%/20% acetone in water (v/v); Fructose-to-Amberlyst resin=1/1 (w/w); mixed at 500 rpm. Key: ■=fructose conversion; ●=HMF yield.

As shown in FIG. 3, the reaction can also be run using solid acid catalysts. FIG. 3 shows the results of a reaction in which a feedstock comprising 5 wt % fructose was reacted in the presence of a solid acid catalyst (Amberlyst®-70 brand sulfonic acid-type resin). The reaction was run at 125° C., in a solvent system comprising 80%/20% acetone in water (v/v). The Amberlyst 70 resin was used in a 1:1 (w/w) ratio with the fructose in the feedstock. Key: ■=fructose conversion; ●=HMF yield. The results over the 200 minute reaction were quite good: fructose conversion was 87%, HMF yield was 82% and HMF selectivity was 94%. Also the solid acid catalyst proved quite stable under these reaction conditions. The acid density (milli-equivlents per gram) of the solid acid catalyst before and after the reaction was unchanged (2.4 meq/g). Thus, the reaction can be run using a wide variety of acid catalyst, including organic acids, mineral acids, as well as heterogeneous solid acid catalysts.

Figure 4:
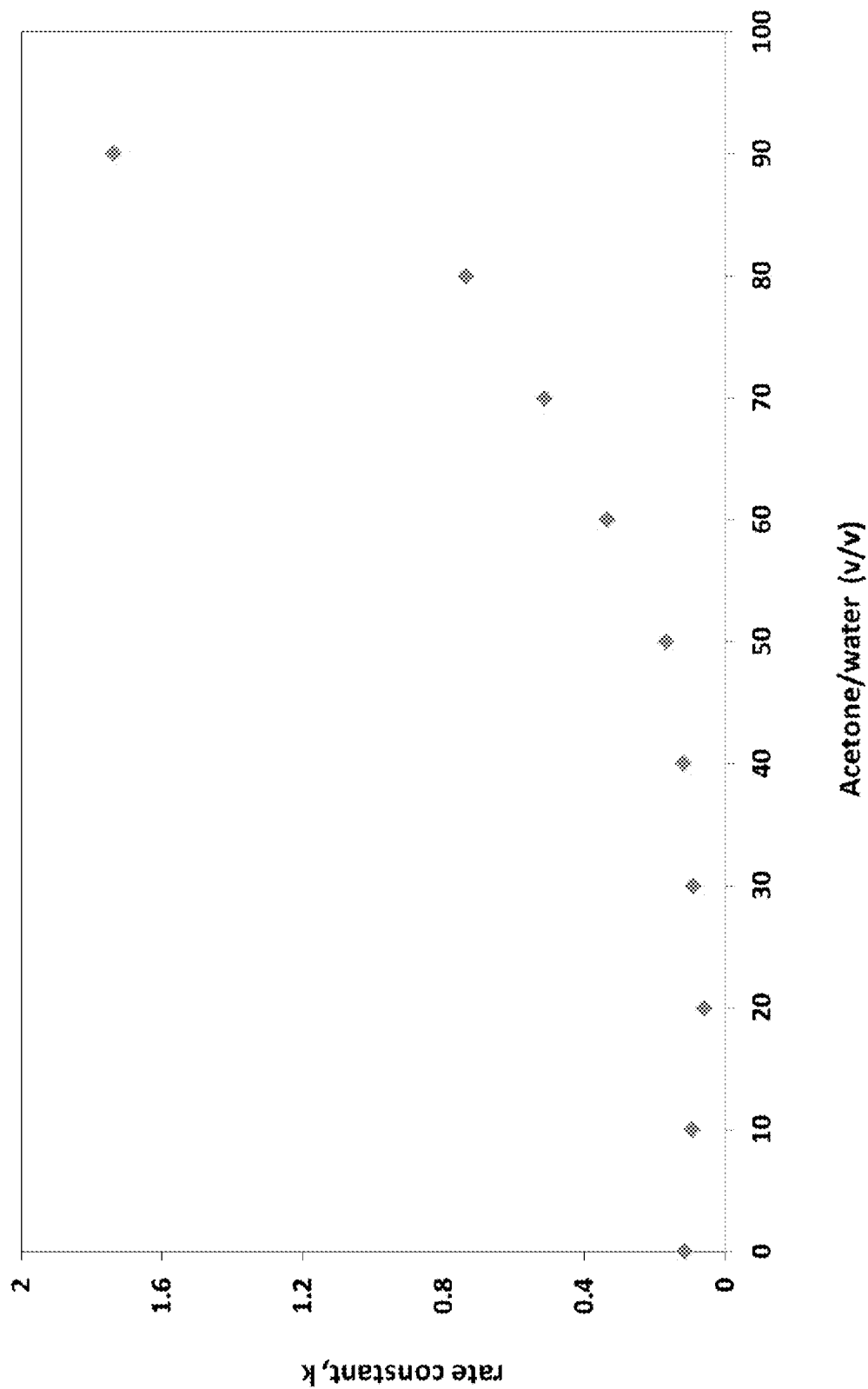
FIG. 4 is a graph showing the effect of acetone concentration on the kinetics of fructose dehydration using the disclosed method. The Y-axis shows rate of dehydration in moles/sec. The X-axis shows concentration of acetone in water (v/v) of the solvent system used. Reaction conditions: 120° C.; reactant was 5 wt % fructose; solvent systems were acetone in water (v/v) varying from pure water (0% acetone) to 90% acetone in water (v/v); 15 mM HCl; mixed at 500 rpm.

FIG. 4 demonstrates that the solvent system chosen for the reaction has a profound effect on the rate of the reaction. Here, a series of reactions were conducted using a feedstock comprising 5 wt % fructose. All of the reactions were conducted at 120° C. and 15 mM HCl, with vigorous mixing. Ten separate reactions were conducted under these same conditions, with the only variable being the solvent system. The solvent system used was acetone in water (v/v) varying from pure water (0% acetone) to 90% acetone in water (v/v). As can be seen in FIG. 4, the reaction rate was flat and even dropped a bit as the acetone concentration was ramped from 0 to about 40% (v/v). But at 50% acetone, the rate started to increase and increased in a marked fashion up to 90% acetone.

Ideally for economic considerations, the reaction would be run at much higher feedstock concentrations. Feedstock concentration, however, is limited by the solubility of C6 carbohydrates in the solvent system. For example, the solubility of fructose in 80/20 acetone/water (v/v) is about 50 g/L at 120° C. (data not shown). The feedstock solubility can be increased by running the reaction at higher temperatures. Thus, at 220° C., a feedstock comprising about 33 wt % fructose can be used.

Figure 5:
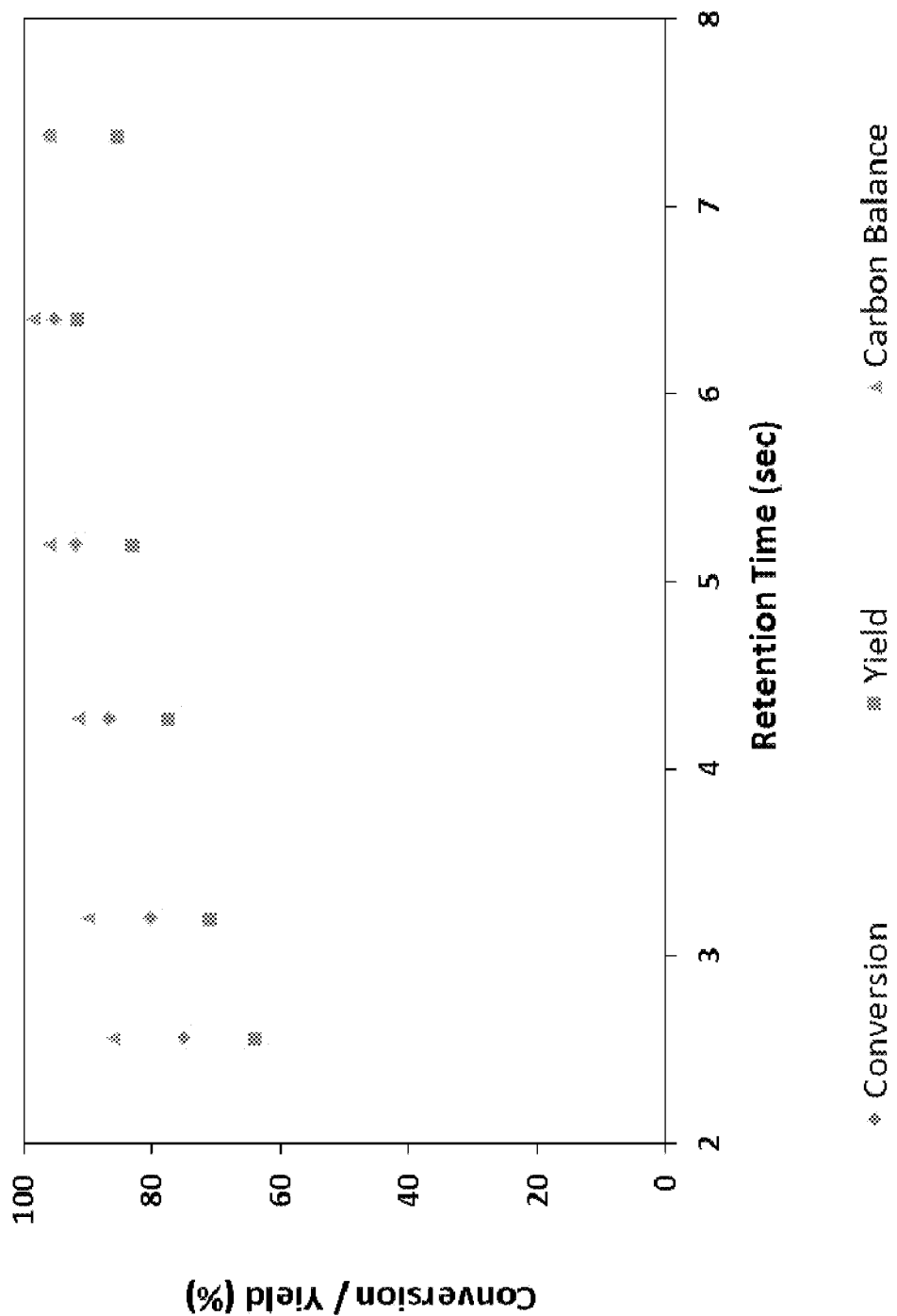
FIG. 5 is a graph showing fructose conversion and fructose concentration over time using the dehydration method disclosed herein with a feedstock comprising 33 wt % fructose. Reaction conditions: 220° C.; reactant was 33 wt % fructose; solvent system was 80%/20% acetone in water (v/v); 15 mM HCl; 600 psi (4.14 MPa) pressure. Key: ▲=carbon balance; ♦=fructose conversion; ■=HMF yield.

Thus, as shown in FIG. 5, a series of reactions were conducted at this higher temperature (220° C.) and at high fructose concentration (33 wt %). As shown in FIG. 5, the reaction performed extremely well under these conditions. FIG. 5 records the fructose conversion and fructose concentration over time for a dehydration reaction using 33 wt % fructose as the feedstock. The reaction was run at 220° C. using an 80%/20% acetone in water (v/v) mixed solvent and 15 mM HCl. The pressure of the reaction was maintained at 600 psi (4.14 MPa). Key: ▲=carbon balance; ♦=fructose conversion; ■=HMF yield. Here, the fructose conversion was a very high 95.3% and the HMF yield was 91.4%. Additionally, at this temperature, the reaction proceeds very quickly. Note that the X-axis in FIG. 5 is measured in seconds, not minutes. As compared to the reaction described for FIGS. 1A and 1B, the reaction described here has a 400× reduction in reactor residence time. In short, the cost of running the reaction at a higher temperature is more than offset by the increased speed of the reaction.

Figure 6:
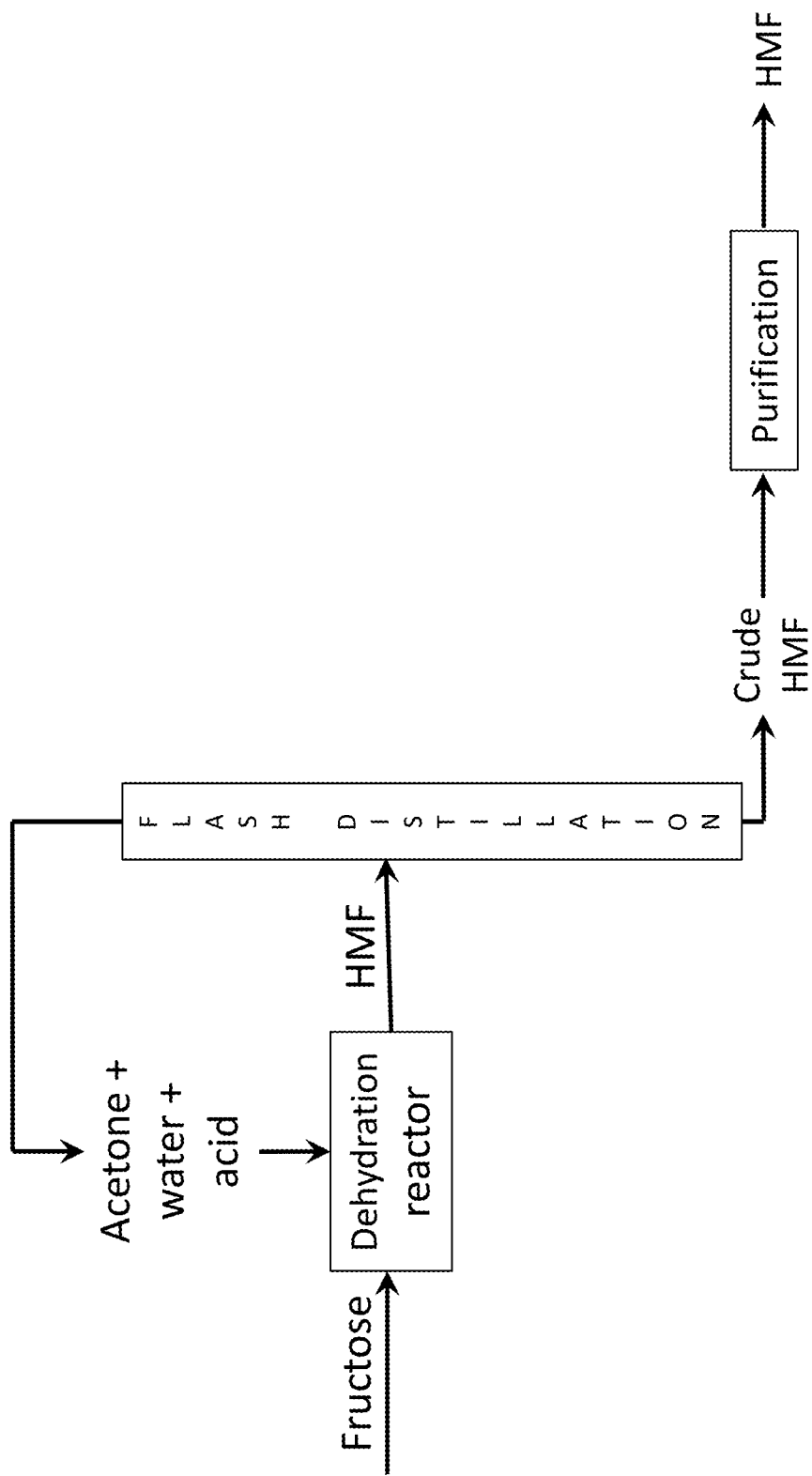
FIG. 6 is a flow chart schematically depicting a first implementation of the method disclosed herein.

The reaction itself can be implemented in a number of different formats, in batch, semi-batch, or continuous fashion. FIG. 6 illustrates a continuous reactor set up in which the acetone/water solvent and a homogeneous acid are recirculated. Working from left-to right across FIG. 6, the feedstock and solvent are introduced into a dehydration reactor at the chosen temperature and residence time. The raw product mix, containing HMF, unreacted reactant, and any by-products are transferred to a separator, shown as a flash distillation column or flash drum in FIG. 6. The flash distillation column shown in FIG. 6 is exemplary; any type of separator dimensioned and configured to separate or enrich the HMF from the other compounds present in the crude product mixture may be used, including traditional distillation columns, vacuum distillation columns, liquid chromatography columns, gas chromatography columns and the like. The acetone/water mix has a much lower boiling point than does the product HMF, and thus is flashed into vapor and is recirculated back into the dehydration reactor. The crude HMF products is tapped off from the bottom of the flash distillation apparatus and optionally may be further purified (if desired or necessary for the chosen end use).

Figure 7:
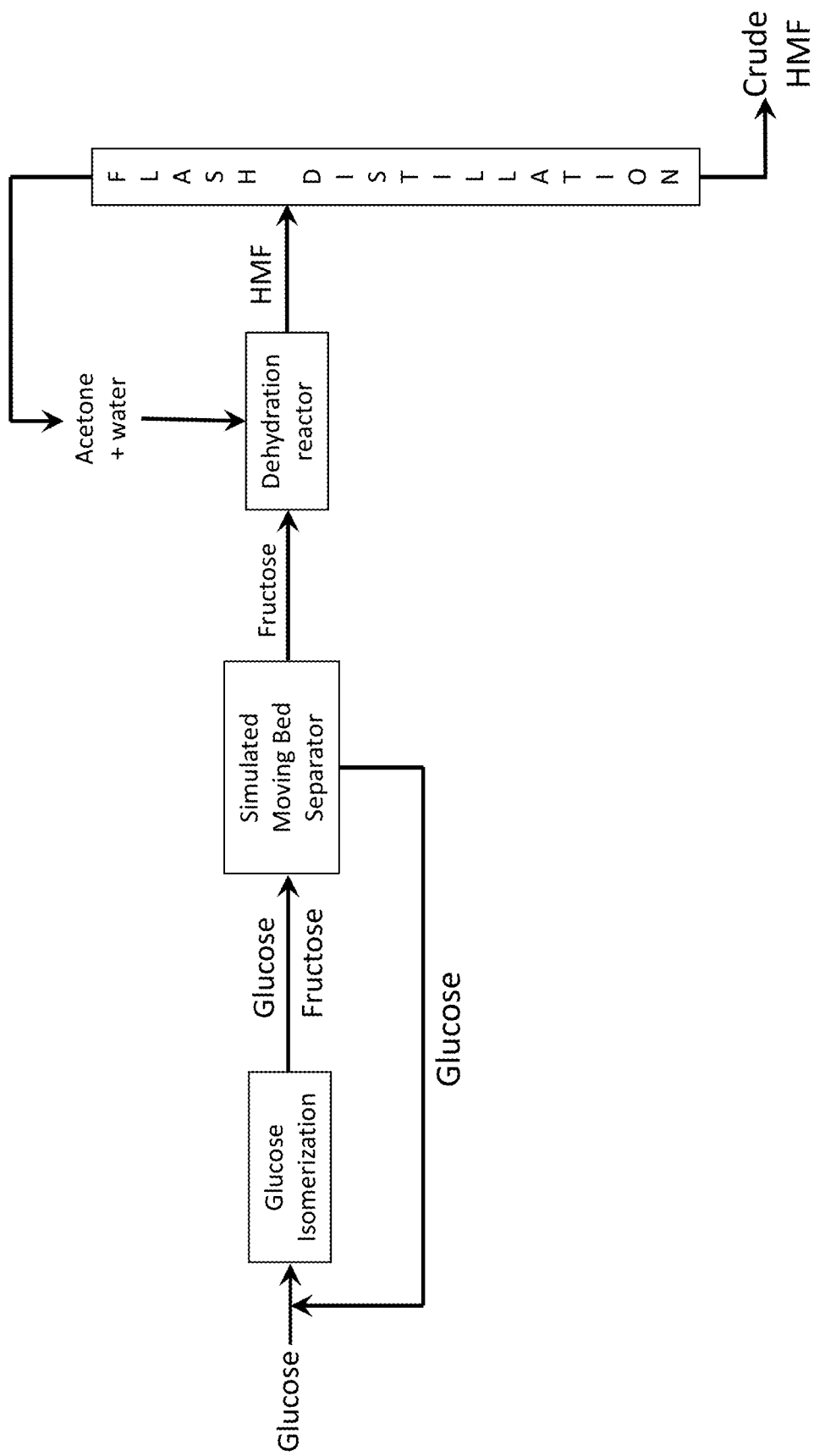
FIG. 7 is a flow chart schematically depicting a second implementation of the method disclosed herein.

Because the preferred reactant is fructose, the reaction can be integrated into the convention route for making high-fructose corn syrup. This is illustrated schematically in FIG. 7. The right-hand side of FIG. 7 is identical to FIG. 6: the feedstock comprising fructose is reacted in a dehydration reactor; the raw product is then separated in a separator (again shown as a flash distillation apparatus at the far right of FIG. 6). The solvent and acid are recycled back into the dehydration reactor as described for FIG. 6. The left-hand side of FIG. 7 schematically illustrates the basic, conventional steps in the manufacture of high-fructose corn syrup. Here, glucose is isomerized into a mixture of glucose and fructose. The fructose concentration is increased further in a downstream separator, shown is a simulating moving bed separator in FIG. 7. The recovered glucose is recycled to the first step of the reaction (to be isomerized into fructose). The resulting stream of fructose is then used as the feedstock in the present method.

Figure 8:
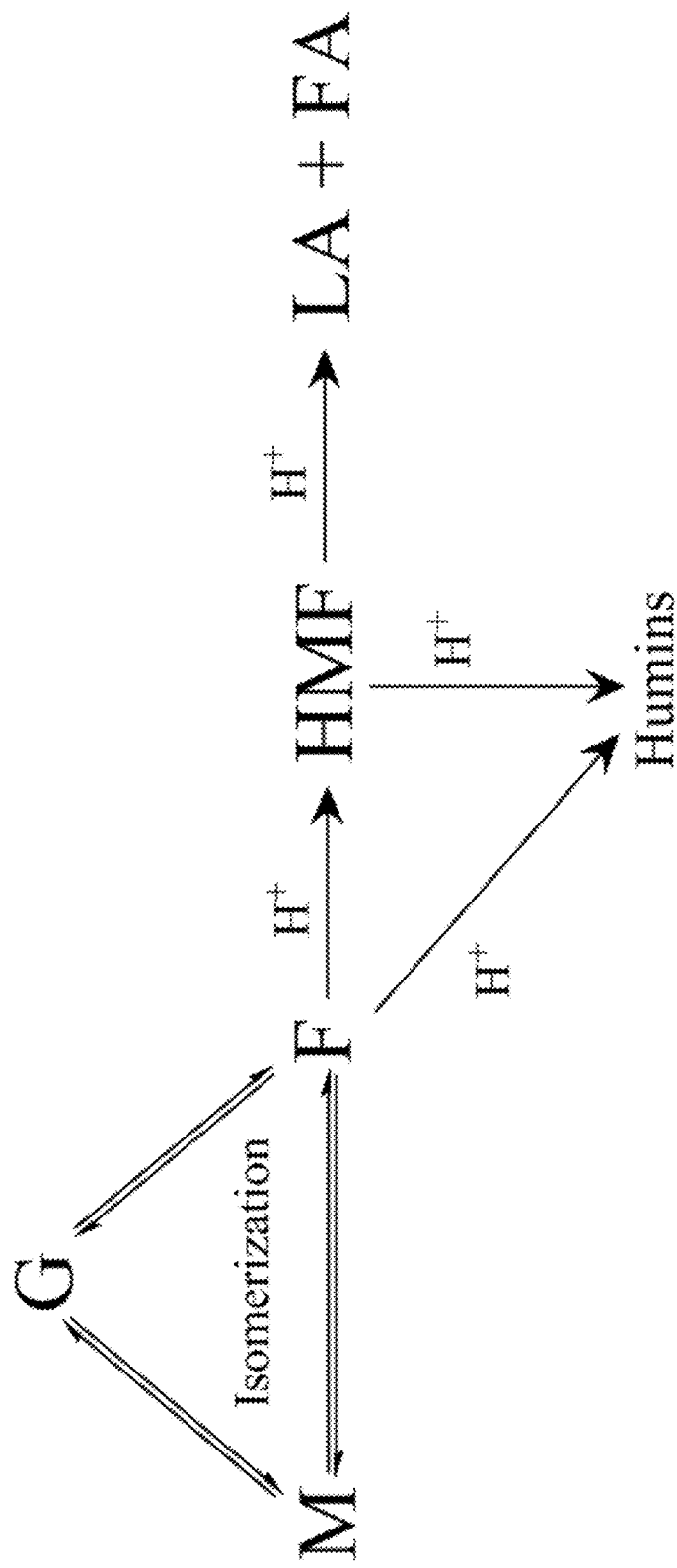
FIG. 8 is a schematic reaction scheme illustrating the isomerization between mannose (M), glucose (G) and fructose (F) and how to capitalize upon the isomerization to drive the product of value-added HMF as contrasted to valueless humins.

Because the high-fructose corn syrup market is mature (with ample capacity and infrastructure), it is economically feasible to practice the method disclosed herein using glucose or mixtures of glucose and fructose as the starting material. This is shown schematically in FIG. 8. The triangular reaction at the left-hand side of the figure illustrates the isomerization between glucose (G), fructose (F) and mannose (M). By driving the isomerization to fructose, the resulting fructose can be tapped off from an initial isomerization reactor and subjected to the method disclosed herein to yield HMF. The resulting HMF can be used as a platform chemical to make other, value-added materials, such as levulinic acid (LA) and formic acid (FA).

Figure 9:
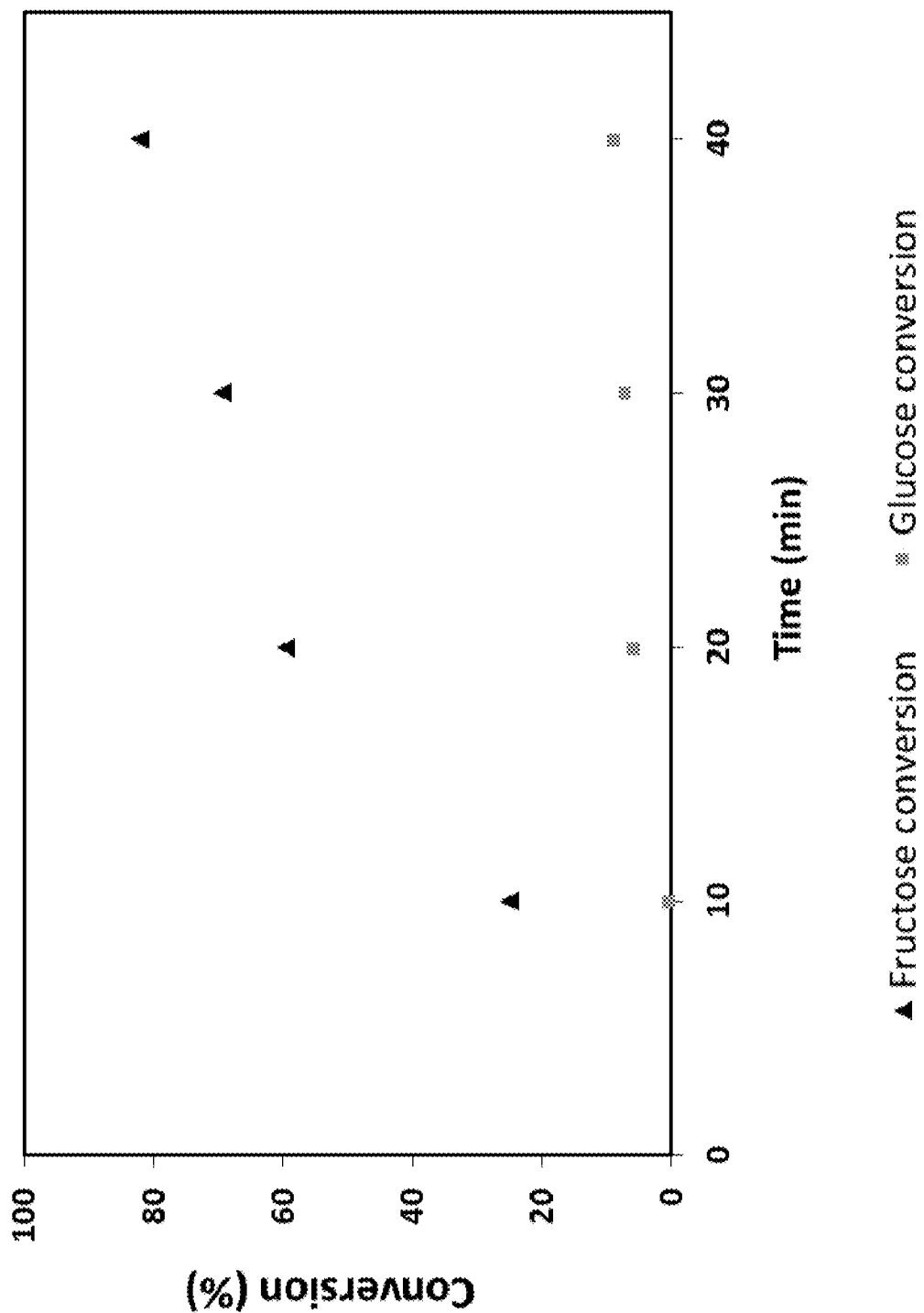
FIG. 9 is a graph depicting the results for dehydration of a mixture of fructose and glucose according to the method disclosed herein. Reaction conditions: 125° C.; initial glucose concentration 55 mM; initial fructose concentration 55 mM; solvent system was 80%/20% acetone in water (v/v); 15 mM HCl; mixed at 500 rpm. Key: ▲=fructose conversion; ■=glucose conversion.
Figure 10:
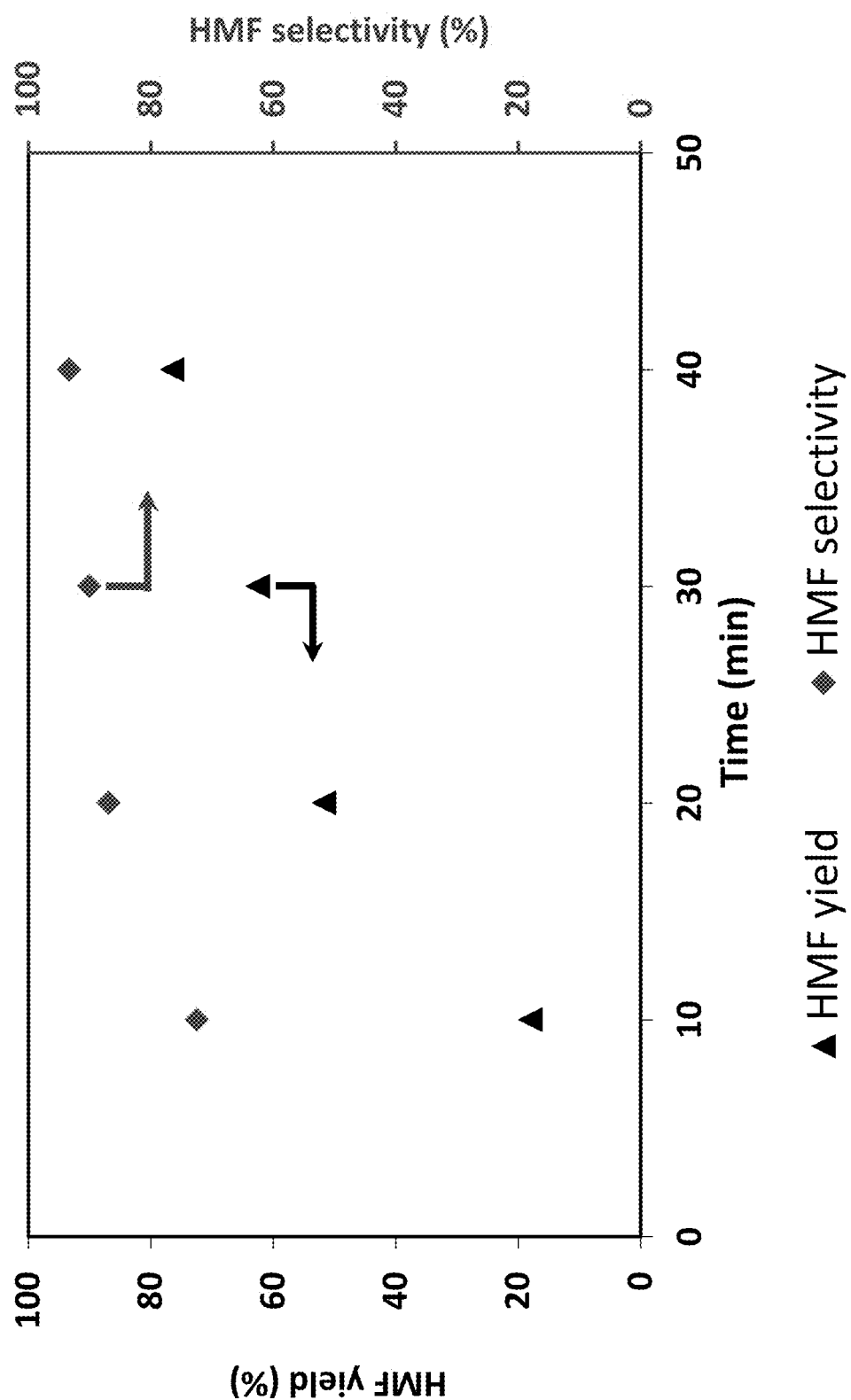
FIG. 10 is a graph showing HMF yield (%) and HMF selectivity (%) over time for the reaction described in FIG. 9. Key: ▲=HMF yield; ♦=HMF selectivity. This graph is particularly notable because HMF yield and selectivity were similar to the reaction in the absence of glucose. HMF yield and selectivity are based on fructose conversion. (Compare with FIG. 2.)

This approach was shown to be practical as illustrated in FIG. 9. In this proof-of-concept reaction, a feedstock comprising an initial glucose concentration 55 mM and an initial fructose concentration 55 mM was reacted at 125° C. The solvent system was 80%/20% acetone in water (v/v) and 15 mM HCl and the reaction was run for 40 minutes. Key: ▲=fructose conversion; ■=glucose conversion. The results of this reaction were surprisingly quite good: fructose conversion was 85% and glucose conversion was only 7%. HMF yield and HMF selectivity for this reaction are shown in FIG. 10. Key: ▲=HMF yield; ♦=HMF selectivity. The results shown in FIG. 10 are also surprising because HMF yield and selectivity were similar to the reaction in the absence of glucose. (Compare with FIG. 2.) Here, selectivity of the reaction to HMF was above 90% (♦) and HMF yield was just shy of 80% (▲).

Figure 11:
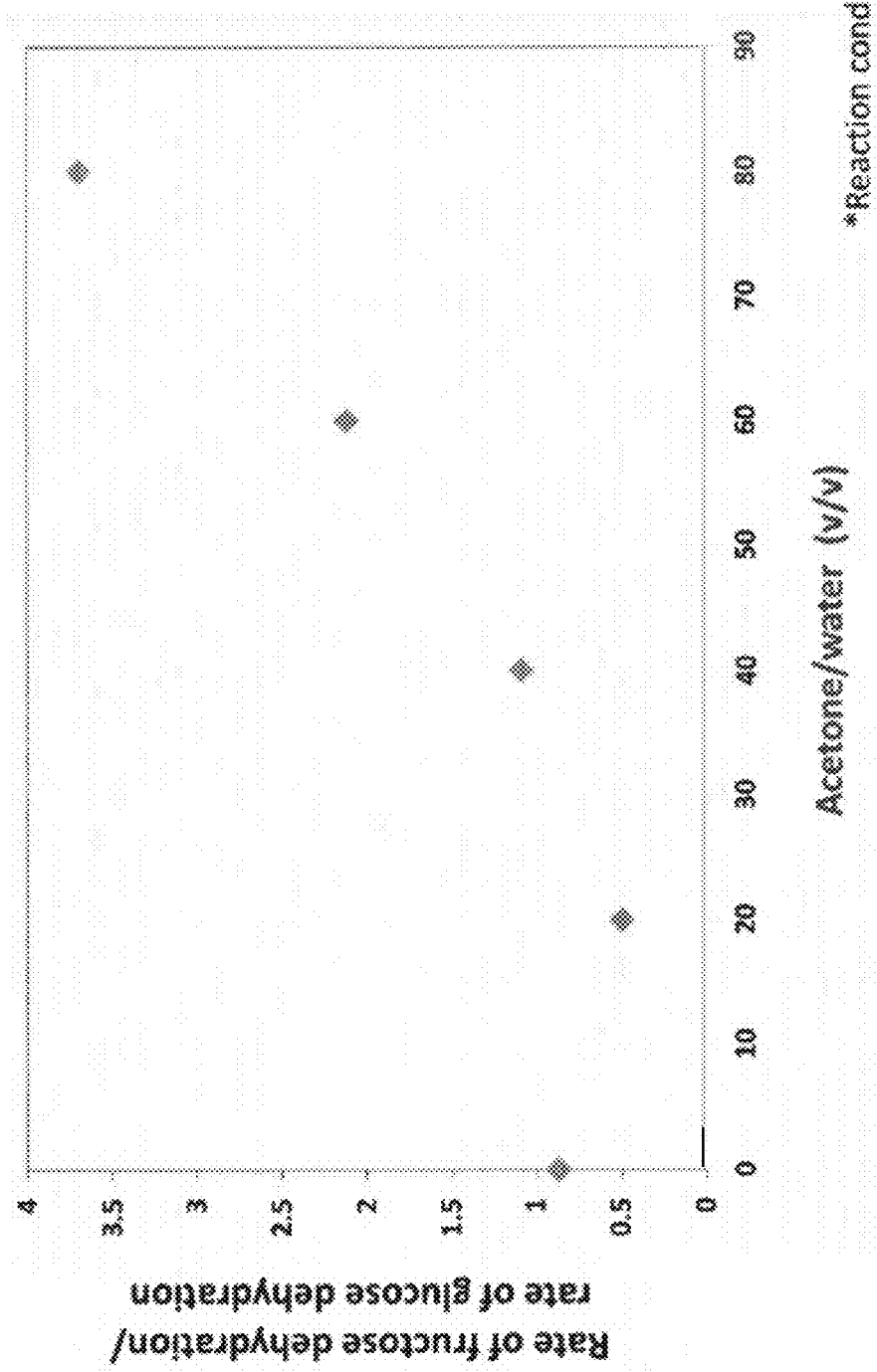
FIG. 11 is a graph showing the effect of acetone concentration on the kinetics of combined glucose/fructose dehydration using the disclosed method. The Y-axis shows the ratio of rate of fructose dehydration/rate of glucose dehydration. The X-axis shows concentration of acetone in water (v/v) of the solvent system used. Reaction conditions were the same as noted in FIG. 9, with the exception that the reactions were conducted at 120° C. The solvent systems were acetone in water (v/v) varying from pure water (0% acetone) to 90% acetone in water (v/v).
Figure 12:
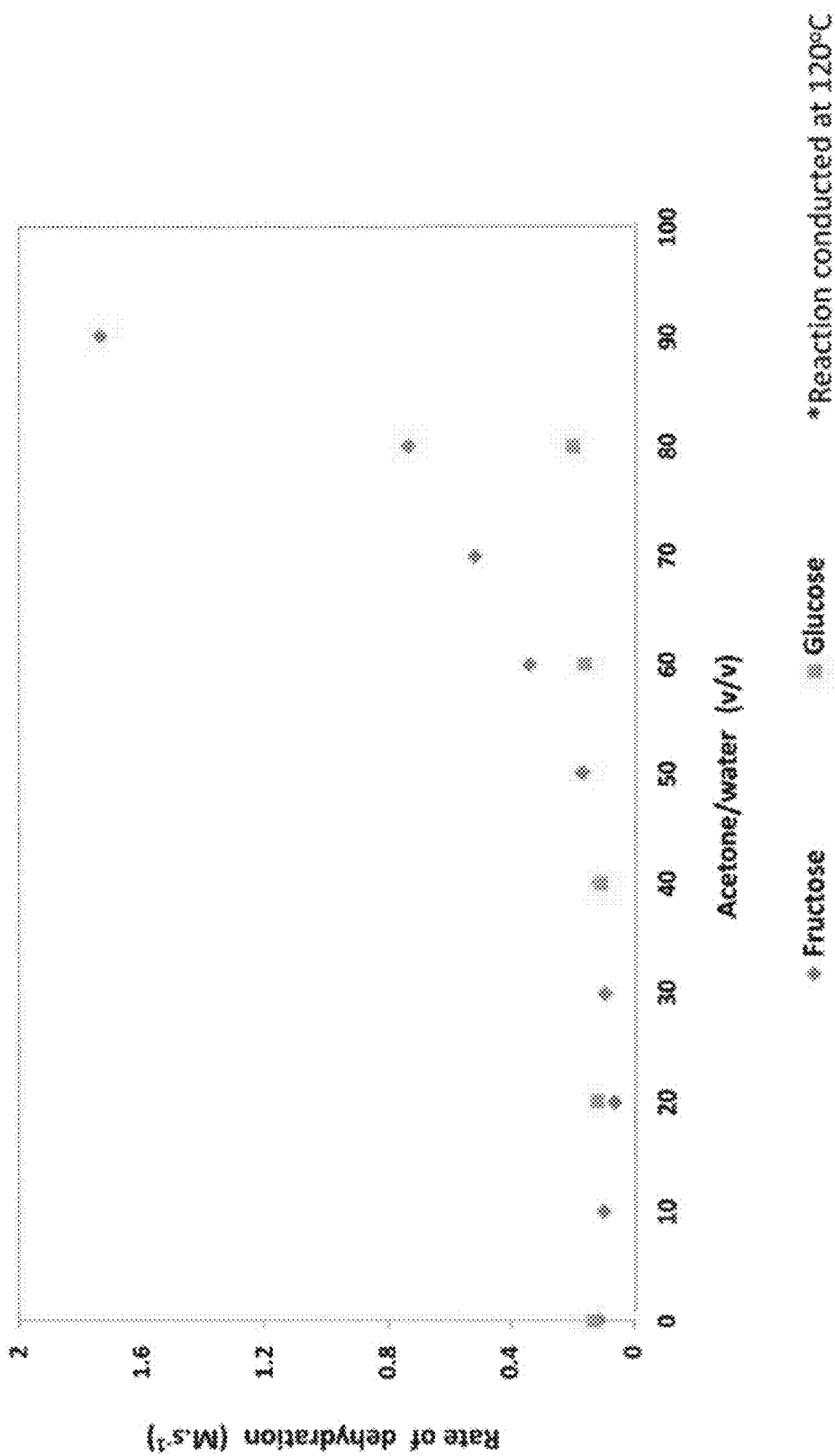
FIG. 12 is a graph analogous to FIG. 11, but breaks out the rates of dehydration for fructose (♦) and glucose (■). Again, the solvent systems were acetone in water (v/v) varying from pure water (0% acetone) to 90% acetone in water (v/v). The rate of glucose dehydration remains flat. In contrast, the rate of fructose conversion vastly increases with an increase of acetone in the solvent system.

As shown in FIG. 11, the solvent effects on the kinetics of the dehydration reaction using a mixture of glucose and fructose as the feedstock mirrored those when using fructose alone. The ratio of fructose conversion to glucose conversion increased to almost 4-to-1 when an 80/20 acetone/water (v/v) solvent system was used. The individual rates of dehydration for fructose vs. glucose are broken out and shown individually in FIG. 12. FIG. 12 is highly significant because it shows that the rate of glucose dehydration is essentially indifferent to the solvent system. The rate of glucose dehydration remained flat regardless of the amount of acetone used in the solvent system. In very stark contrast, the rate of fructose conversion vastly increased with the increase of acetone in the solvent system.

The method can also be implemented using high-fructose corn syrup without separating the glucose from the feedstock or otherwise enriching the high-fructose corn syrup in fructose. For example, using a feedstock containing 45 wt % glucose, the glucose is isomerized to fructose and the resulting high-fructose corn syrup dehydrated according to the present method at, for example, 220° C., 15 mM acid, in 80/20 acetone/water (v/v/). At about 220° C., the residence time in the reactor is very short, on the order of 5 to 10 seconds. The low residence time in the reactor, coupled with a high carbohydrate concentration in the feedstock, are very attractive advantages. Simulations of this reaction predict that using an initial feedstock of 45 wt % glucose would yield an ultimate glucose conversion of about 48%, a fructose conversion of about 97%, an anhydo sugar+oligomeric sugar yield of about 50%, and an HMF yield (from glucose) of about 92%. Total carbon balance is quite good at roughly 98%.

Figure 13:
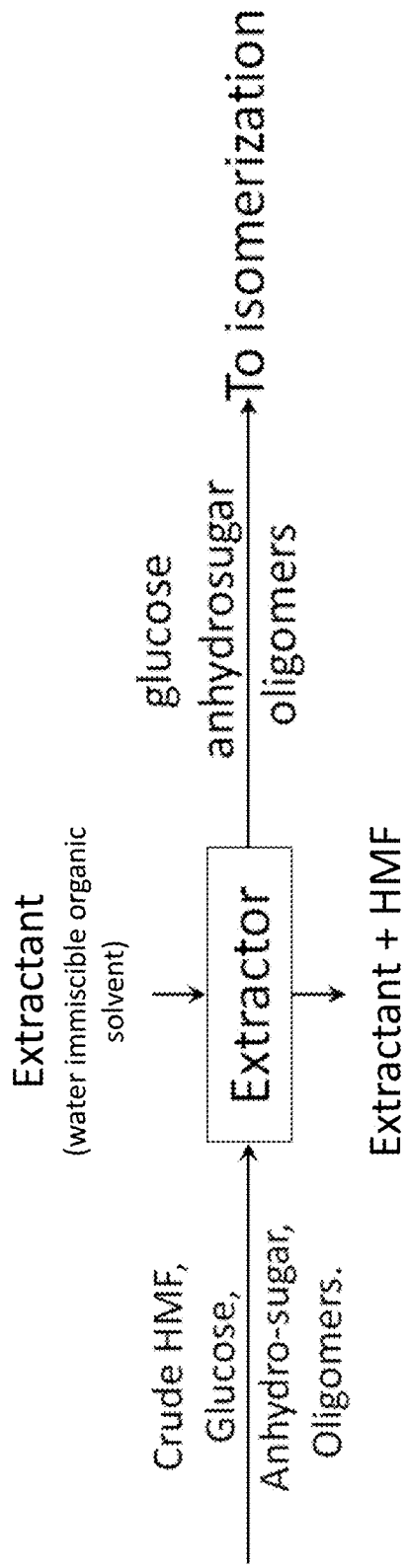
FIG. 13 is a flow chart schematically illustrating one approach for separating product HMF from unreacted sugars and reaction by-products.

FIG. 13 is a flow chart schematically illustrating the process immediately post-dehydration reaction and after removal of much of the solvent. The crude product mixture contains HMF, unreacted glucose, anhydro-sugars, and oligomeric sugars. The HMF product solidifies along with the sugars after complete solvent removal. The solid crude product is then extracted using a suitable extraction solvent, such as methyl isobutyl ketone (MIBK). MIBK is chosen as an example as it is essentially immiscible with water and has very high HMF solubility. HMF purity after extraction with MIBK is about 96% (determined by HPLC). As shown in FIG. 13, the glucose and other sugars can be recycled back to isomerization unit and passed through subsequent rounds of dehydration reaction.

Figure 14:
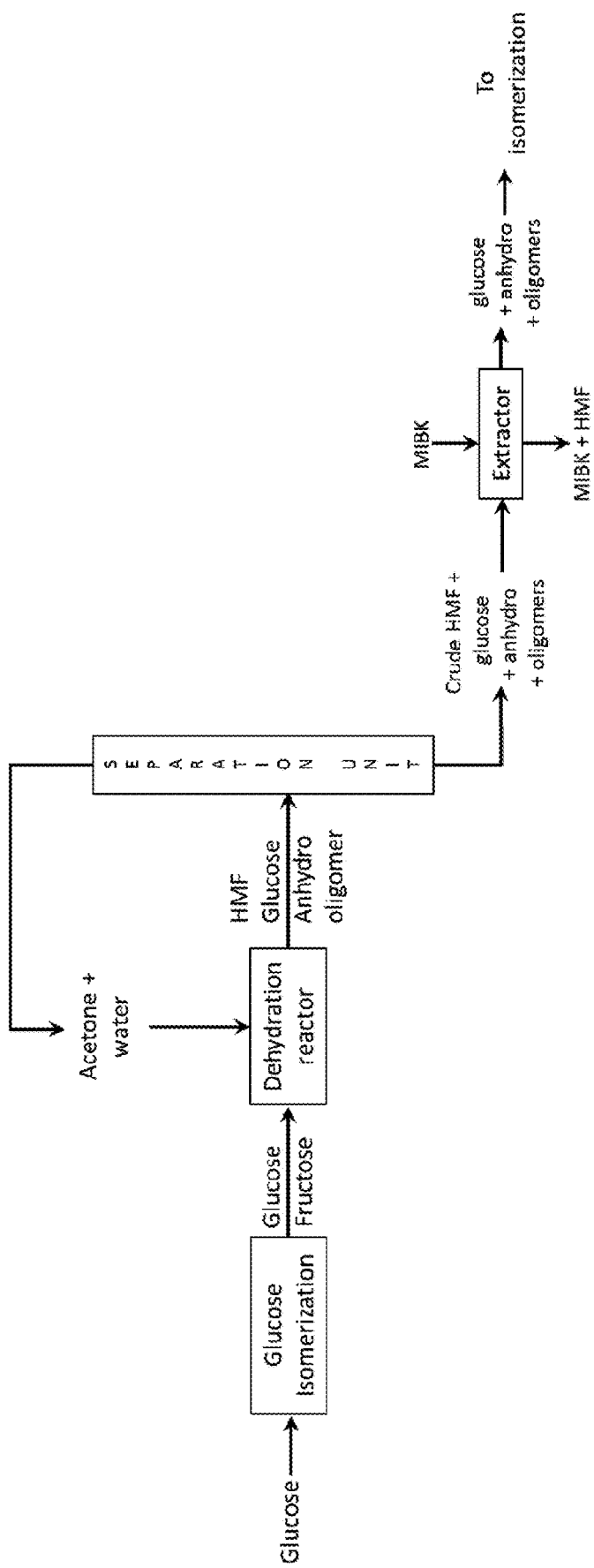
FIG. 14 is a flow chart schematically depicting a third implementation of the method disclosed herein using high-fructose corn syrup as the feedstock.

The entire process starting from glucose and without separation of glucose from the high-fructose corn syrup feed is illustrated schematically in FIG. 14. Starting from the left-hand side of the figure, an initial high-concentration glucose feedstock is subjected to isomerization to yield high-fructose corn syrup. Without any further processing of the high-fructose corn syrup, it is subjected to dehydration as described herein in a dehydration reactor. The solvent in the crude product exiting the dehydration reactor is removed, preferably by flash distillation, as shown in the figure. The solvent is recirculated back into the dehydration reactor. The crude HMF-containing product mixture is then extracted with MIBK to yield the final HMF product. (The MIBK can be removed from the HMF via any suitable means, such as vacuum distillation.) The by-products (unreacted glucose, anhydro sugars and sugar oligomers) are recycled back into the reaction to be isomerized into fructose and again subjected to dehydration as described herein.

Figure 15:
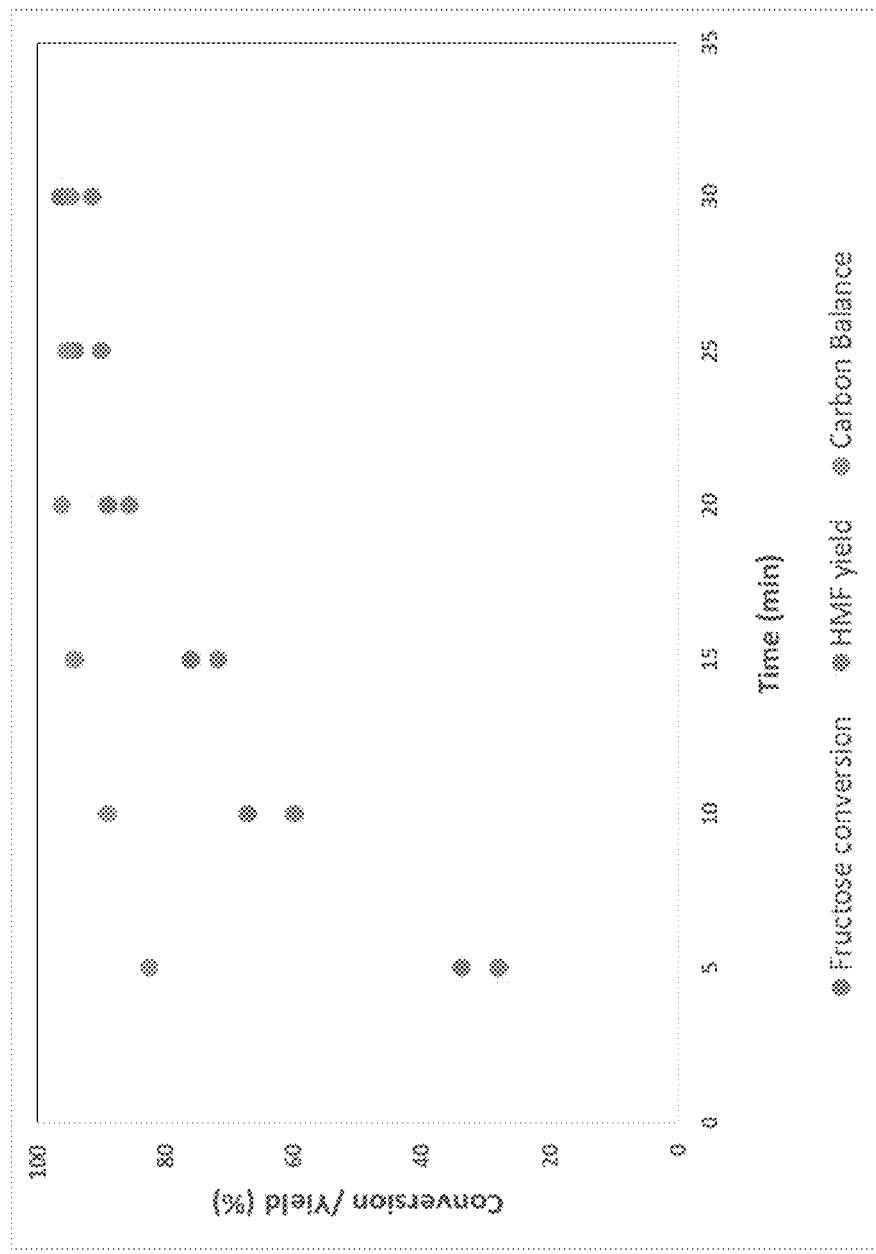
FIG. 15 is a graph showing fructose conversion (blue circles), HMF yield (orange circles), and carbon balance (grey circles) over time using the dehydration method disclosed herein with a feedstock comprising 25 wt % fructose. Reaction conditions: 125° C.; reactant was 25 wt % fructose; solvent system was 80%/20% acetone in water (v/v); 100 mM HCl; autonomous pressure.

FIG. 15 is a graph showing the results of reacting 25 wt % fructose at 125° C., in a solvent system consisting of 80%/20% acetone in water (v/v) and 100 mM HCl. Fructose conversion is shown in blue circles. HMF yield is shown in orange circles. Carbon balance is shown in grey circles. Reaction residence time is shown on the X-axis. As can be seen from FIG. 15, at about 20 minutes reactor residence time, the carbon balance achieves a maximum. Conversion and HMF yield also near their maxima at about 20 minutes. The reaction data at 5-minute intervals is shown in Table 2:

TABLE 2

Fructose Dehydration - Effect of Reactor Residence Time

| Residence time (min) | Conversion (%) | HMF (%) | Carbon Balance |
|---|---|---|---|
| 5 | 33.92 | 28.04 | 82.67 |
| 10 | 67.17 | 59.93 | 89.21 |
| 15 | 76.23 | 71.85 | 94.26 |
| 20 | 89.02 | 85.77 | 96.34 |
| 25 | 94.32 | 90.11 | 95.54 |
| 30 | 96.44 | 91.50 | 94.88 |

As shown in Table 2, under these conditions, the optimal residence time in the reactor was about 20 minutes. At these conditions, the carbon balance conversion and HMF yield all were excellent.

What is claimed is:

1. A method to produce 5-hydroxymethylfurfural (HMF), the method comprising:
reacting a reactant comprising at least 25 wt % of at least one C6 carbohydrate, in a reaction mixture comprising about 25% (v/v) to about 5% water, about 75% (v/v) to about 95% (v/v) polar, aprotic solvent, and an acid, for a time, at a temperature, and at a hydrogen ion concentration wherein at least a portion of the C6 carbohydrate present in the reactant is converted to 5-hydroxymethylfurfural (HMF), wherein the polar, aprotic solvent is a ketone.

2. The method of claim 1, wherein the polar, aprotic solvent is selected from aliphatic ketones, cyclic ketones, and aryl ketones.

3. The method of claim 1, wherein the polar, aprotic solvent is selected from the group consisting of di-$C_1$-$C_6$-alkyl ketones.

4. The method of claim 1, wherein the polar, aprotic solvent is acetone.

5. The method of claim 1, wherein the polar, aprotic solvent is present in a concentration of about 80% (v/v) in water.

6. The method of claim 1, wherein the acid is present in an amount to yield a hydrogen ion concentration in the reaction mixture of from about 1 mM to about 500 mM.

7. The method of claim 1, wherein the acid is present in an amount to yield a hydrogen ion concentration in the reaction mixture of from about 5 mM to about 100 mM.

8. The method of claim 1, wherein the acid is present in an amount to yield a hydrogen ion concentration in the reaction mixture of from about 5 mM to about 50 mM.

9. The method of claim 1, wherein the acid is a Brønsted-Lowry Acid.

10. The method of claim 1, wherein the acid is a mineral acid.

11. The method of claim 1, wherein the acid is a solid acid catalyst.

12. The method of claim 1, wherein the acid is an organic acid.

13. The method of claim 1, wherein the temperature is from about 80° C. to about 300° C.

14. The method of claim 1, wherein the temperature is from about 80° C. to about 250° C.

15. The method of claim 1, wherein the temperature is from about 80° C. to about 220° C.

16. The method of claim 1, wherein the temperature is from about 100° C. to about 200° C.

17. The method of claim 1, wherein the at least one C6 carbohydrate comprises fructose.

18. The method of claim 1, wherein the reactant comprises at least one C6 carbohydrate selected from the group consisting of fructose, glucose, and mannose.

\* \* \* \* \*